United States Patent [19]

Della Valle et al.

[11] Patent Number: 5,709,877

[45] Date of Patent: *Jan. 20, 1998

[54] GELS IN THE FORM OF HIGHLY HYDRATED SELF-SUPPORTING FILM, THE PROCESS FOR THEIR PREPARATION, AND THEIR USE IN THE THERAPY OF CUTANEOUS LESIONS AND/OR PATHOLOGIES

[75] Inventors: Francesco Della Valle; Alessandro Rastrelli, both of Padua; Gabriella Calderini, Carrara San Giorgio; Aurelio Romeo, Rome, all of Italy

[73] Assignee: Fidia S.p.A., Abano Terme, Italy

[*] Notice: The term of this patent shall not extend beyond the expiration date of Pat. No. 5,523,093.

[21] Appl. No.: 476,569

[22] Filed: Jun. 7, 1995

Related U.S. Application Data

[63] Continuation of Ser. No. 707,790, May 30, 1991, Pat. No. 5,523,093.

[30] Foreign Application Priority Data

May 30, 1990 [IT] Italy .................................. 20477A90

[51] Int. Cl.⁶ .................... A61K 9/70; A61K 47/36; A61L 15/28; A61L 15/64
[52] U.S. Cl. ............... 424/444; 424/488; 424/DIG. 13; 602/41; 602/48; 602/49; 602/52; 252/315.3; 252/315.4; 514/777; 514/779; 514/944
[58] Field of Search ................... 424/484, 78.02, 424/78.06, 78.07, 78.38, DIG. 13, 443–44, 488; 602/41, 48–49, 52; 252/315.3, 315.4; 106/205

[56] References Cited

U.S. PATENT DOCUMENTS

| | | | |
|---|---|---|---|
| 2,512,616 | 6/1950 | Eberl et al. | 424/445 |
| 3,640,741 | 2/1972 | Etes | 424/401 |
| 4,391,799 | 7/1983 | Mason, Jr. et al. | 514/779 |
| 4,443,538 | 4/1984 | Cheetham | 435/182 |
| 4,524,064 | 6/1985 | Nambu | 424/81 |
| 4,844,902 | 7/1989 | Grohe | 424/449 |
| 4,948,575 | 8/1990 | Cole et al. | 424/445 X |
| 5,071,741 | 12/1991 | Brockbank | 436/18 |
| 5,194,253 | 3/1993 | Garrido | 424/78.03 |

FOREIGN PATENT DOCUMENTS

| | | |
|---|---|---|
| A-0095892 | 7/1983 | European Pat. Off. . |
| A 492264 | 9/1938 | United Kingdom . |
| A1329693 | 9/1973 | United Kingdom . |
| WO-A9002774 | 3/1990 | WIPO . |

*Primary Examiner*—Edward J. Webman
*Attorney, Agent, or Firm*—Birch, Stewart, Kolasch & Birch, LLP

[57] ABSTRACT

This invention provides new gels in the form of highly hydrated self-supporting film, comprising one or more alkaline alginates, an alkaline earth alginate, a polyalcohol and a natural, synthetic or semisynthetic polymer of hydrophilic nature, and their preparation process. These polysaccharide-matrix gels in highly hydrated self-supporting film form are suitable for use as covering and protection materials for cutaneous lesions and/or pathologies in that they are obtainable in self-supporting form in the desired thickness, are transparent, flexible, have good mechanical characteristics, are adaptable to the lesion surface without strongly adhering to it, and are permeable to gas but are impermeable to liquids and bacteria; one or more pharmacologically active substances can also be incorporated in the gel.

35 Claims, 1 Drawing Sheet

GELS IN THE FORM OF HIGHLY HYDRATED SELF-SUPPORTING FILM, THE PROCESS FOR THEIR PREPARATION, AND THEIR USE IN THE THERAPY OF CUTANEOUS LESIONS AND/OR PATHOLOGIES

This application is a continuation of application Ser. No. 07/707,790, filed on May 30, 1991, now U.S. Pat. No. 5,523,093, the entire contents of which are hereby incorporated by reference.

FIELD OF THE INVENTION

This invention relates to new gels in the form of highly hydrated self-supporting film, the process for their preparation and their use in the therapy of cutaneous lesions and/or pathologies.

PRIOR ART

Hydrogels consisting of synthetic or semisynthetic polymers or synthetic polymers with small additions of natural polymers and having the characteristic of being only slightly or not reabsorbable are already known for the treatment of cutaneous lesions.

Xerogels, i.e. anhydrous gels consisting of fibres of calcium alginate presented in the form of bioreabsorbable unwoven tissue, are also known.

Protective films of various types used for treating cutaneous lesions are also known.

For example, DE patent 30 17 221 describes an ointment containing a soluble alkaline metal alginate salt which when applied to the lesion and treated in situ with a soluble calcium salt forms a protective film of Ca alginate. To obtain this film the ointment must be reconstituted at the moment of use.

WO patent 80/02300 describes the process for preparing an unwoven tissue based on calcium alginate fibres.

U.S. Pat. No. 4,393,048 describes a gel containing an alkaline metal alginate and glycerol for wound medication which on drying forms a protective adhering film, and U.S. Pat. No. 4,391,799 describes the same gel in association with silver salts for treating white phosphorus burns.

European patent application EPA 83301149.7 describes wound medications in the form of hydrogel membranes composed of hydrophilic biopolymers derived from keratin, glycosaminoglycan or collagen.

U.S. Pat. No. 4,664,105 describes a wound medication composed of granulated cellulose material or a polysaccharide.

Gels in the form of highly hydrated self-supporting alginate-based film have never been described.

An object of the present invention is to provide a wound medication in the form of a thin self-supporting film which maintains a high degree of hydration for a prolonged time, this being of known and considerable importance for the repair to take place in a short time and within the dictates of the process physiology, to result in cicatrices with optimum characteristics both from the physiological and from the aesthetic aspect.

A further object of the present invention is to provide a wound medication in the form of a bioreabsorbable film, this characteristic allowing the medication to be replaced at a much lesser rate, thus avoiding further irritation to the lesion and facilitating the reparative process.

A further object of the invention is to provide a wound medication in the form of a film with good mechanical characteristics which is soft, pliable, easily handled and properly adaptable to the lesion, but which is only slightly adhesive and can therefore be easily removed without damaging the newly formed tissues, and further which is non-toxic, sterilizable in an autoclave and by gamma rays, compatible with a large number of drugs, therefore allowing their incorporation, does not need to be reconstituted at the moment of use, can absorb exudates, is permeable to gases but not to liquids or bacteria, and which is transparent to enable the development of the reparative process to be followed.

A further object of the invention is to provide a medication which is economically valid in that it reduces the number of medications required.

SUMMARY OF THE INVENTION

These and further objects are attained by the composition according to the present invention, which relates to new gels characterised by being in the form of highly hydrated self-supporting film comprising one or more alkaline alginates, an alkaline earth alginate, a polyalcohol and a natural, synthetic or semisynthetic polymer of hydrophilic character. In one embodiment of the invention a medicament is dispersed within the gel. These gels in highly hydrated self-supporting film form are prepared by a new process which together with the use of the new film in the therapy of human lesions and/or pathologies also form part of the invention.

DETAILED DESCRIPTION

Figure 1:
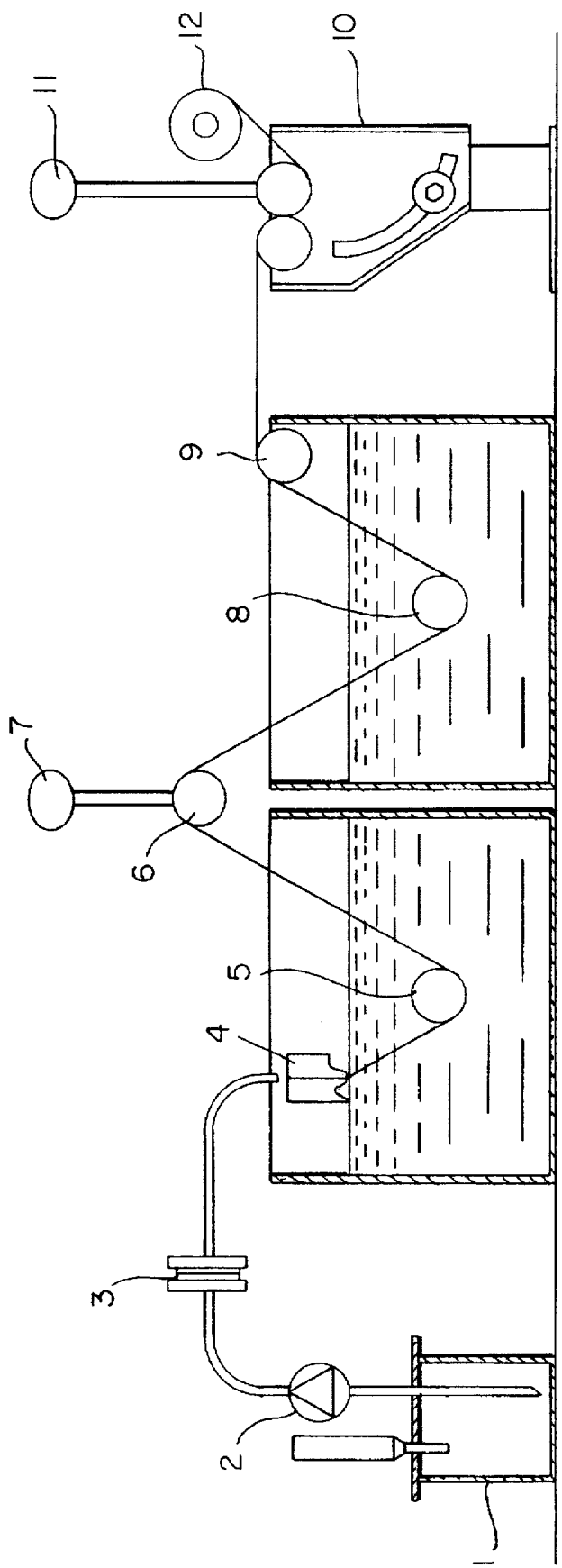
FIG. 1 shows the longitudinal section of a device useful for the preparation of a film according to the present invention.

The gel in highly hydrated self-supporting film form according to the present invention contains a quantity of between 1% and 7.5%, and preferably 3.5%, (all percentages being by weight) of one or more alkaline alginates, preferably sodium alginate; a quantity of between 0.1% and 5%, and preferably 1%, of an alkaline earth alginate, preferably calcium alginate; a quantity of between 0.1% and 10%, and preferably 5%, of a polyalcohol, preferably glycerol; and a quantity of between 0.05% and 10%, and preferably 0.5%, of a natural, synthetic or semisynthetic polymer of hydrophilic character, preferably sodium hyaluronate, plus optionally between about 0.01% and 10% of one or more medicaments, the remainder being water. Other alkaline alginates which can be advantageously used are for example potassium and ammonium alginates.

The described film is obtained with the required characteristics according to the invention by starting from an initial fluid gel containing a quantity of between 3.5% and 7.5%, and preferably 3.5%, of one or more alkaline alginates, preferably sodium alginate, a quantity of between 0.5% and 7.5%, and preferably 5%, of a polyalcohol, preferably glycerol, a quantity of between 0.1% and 10%, and preferably 0.2%, of a natural, synthetic or semisynthetic polymer of hydrophilic character, preferably sodium hyaluronate, plus optionally a medicament.

The initial fluid gel is extruded by pumping through a slit of adjustable width and thickness, and coagulated by passage through between 2 and 4 successive baths, preferably 2, at controlled temperature, the baths containing one or more soluble calcium salts.

The concentration of $Ca^{2+}$ ions in the various coagulation baths is between 0.1 and 10% and preferably 1% in the first coagulation bath, and 2% in the subsequent baths.

The coagulation bath temperature is between 15° C. and 40° C. and preferably 20° C. for the first, and 30° C. for the subsequent baths. After passage through the last coagulation bath a highly hydrated gel is obtained in the form of a self-supporting thin film having a thickness variable between 0.1 and 5 mm, preferably 0.4 mm, with a pH of between 5.5 and 7.5, preferably between 6.5 and 7.2. The final film characteristics, such as its mechanical and hydration characteristics, can be varied according to requirements by varying the initial gel composition and the coagulation bath conditions.

In a preferred embodiment of the process according to the invention, the alginate film is prepared by extrusion and coagulation using the device shown in FIG. 1.

The initial fluid gel is placed in a container vessel 1 from which it is drawn by a pump 2 operating at a suitable r.p.m., then passed through a filter 3 and fed to the filming extruder 4 comprising a slit of suitable variable size immersed in the first coagulation bath.

Coagulation occurs immediately on leaving the filming extruder, the recovered film being passed below a guide drum 5 immersed in the first coagulation bath. The film then leaves the bath, passes through a dragging roller 6 driven by a motor 7, enters a second coagulation bath through which it is guided by a second drum 8, leaves the bath guided by a third drum 9 and is wound onto a winding reel 12 by a calender 10 driven by a motor 11.

The size-setting of the extruder, the pump r.p.m., the dragging roller speed and the winding roller speed can be varied to define the final characteristics of the film.

For example a film according to the present invention with a thickness of 300µ is obtained by using the device of FIG. 1 under the following operating conditions:

pump r.p.m.: 15 r.p.m. equivalent to a throughput of 18 cc/min size setting of filming extruder: 200µ dragging roller r.p.m.: 2.15 r.p.m.

temperature 1st bath ($CaCl_2$ 1% w/v): 20° C.

temperature 2nd bath ($CaCl_2$ 2% w/v): 27° C.

extruded film length produced per minute: 0.4 m.

Any active principle compatible with the gel composition, such as substances of antiseptic, antibiotic, anti-inflammatory, antihistaminic or other activity, can be incorporated into the gel either alone or in association. The concentration of the active principle incorporated into the gel depends on its pharmacological characteristics, and would represent a quantity such as to make it effective for the purpose of the specific application. The medicament quantity in the compositions of the invention can vary from about 0.01% to 10% of the weight of the final product.

The film obtained in this manner can be easily stored, handled and used advantageously as covering or medication material for cutaneous lesions and/or pathologies such as the treatment of wounds of surgical or traumatic origin, burns or lesions of pathological origin such as stasis ulcers, bedsores and the like.

Some non-limiting examples of the preparation of self-supporting film according to the invention are described below.

EXAMPLE 1

24.5 g of sodium alginate are dispersed at ambient temperature in 250 ml of water under continuous stirring. A viscous gel forms, to which are added 1.4 g of sodium hyaluronate Hyalastine fraction (European patent EP 0138572 granted on 25$^{th}$ Jul. 1990), 35 g of glycerol and 7 g of NaCl dissolved in 250 ml of water under stirring, the final solution volume then being adjusted to 700 ml. Slow stirring, to avoid incorporating air, is then continued for about 20 hours, after which the viscous solution is filtered through a 20µ mesh filter and degassed under vacuum.

The solution is extruded by pumping through a slit of width 12 cm and of set thickness, and is coagulated by passing through two successive baths containing calcium chloride, the first at 20° C. with a concentration of 1% and the next at 30° C. with a concentration of 2%. The film obtained, having a thickness of about 0.250 mm, is wound on a suitable spool, washed by immersion in a water bath for 1 hour and finally stored in an aqueous solution containing 5% glycerol, 0.2% methylparaben, 0.02% propylparaben and 0.2% sodium dehydroacetate.

EXAMPLE 2

Following the procedure described in Example 1, 1.4 g of sodium hyaluronate Hyalectine fraction (European patent EP 0138572 granted on 25$^{th}$ Jul. 1990) are added in place of the Hyalastine fraction, to obtain a film having analogous characteristics to those of the film obtained in Example 1.

EXAMPLE 3

50 ml of an aqueous solution containing 0.4 g of hyaluronic acid ethyl ester of 75% esterification (HYAFF 7 p75 European patent application EPA 216453 of 7th Jul. 1986) are added to 150 ml of an aqueous solution containing 7 g of sodium alginate, 10 g of glycerol and 2 g of NaCl. After filtration and degassing, the final solution is extruded and coagulated by the procedure described in Example 1 to obtain 150 g of film with a thickness of 0.250 mm. The film is stored in the solution of glycerol and preservatives described in Example 1.

EXAMPLE 4

50 ml of an aqueous solution containing 5 g of polyethyleneglycol 1500 are added to 150 ml of an aqueous solution containing 7 g of sodium alginate, 10 g of glycerol and 2 g of NaCl. After filtration and degassing, the final solution is extruded and coagulated by the procedure described in Example 1 to obtain 150 g of film with a thickness of 0.250 mm. The film is stored in the solution of glycerol and preservatives described in Example 1.

EXAMPLE 5

50 ml of an aqueous solution containing 2.5 g of p-(aminomethyl) benzenesulphonamide acetate are added to 150 ml of an aqueous solution containing 7 g of sodium alginate, 10 g of glycerol and 2 g of NaCl. After filtration and degassing, the final solution is extruded and coagulated by the procedure described in Example 1 to obtain 150 g of film with a thickness of 0.250 mm. The film is stored in the solution of glycerol and preservatives described in Example 1.

EXAMPLE 6

50 ml of an aqueous solution containing 0.1 g of the neomycin salt of hyaluronic acid partly esterified with ethanol (75% of the carboxyl groups esterified with ethanol, 25% of the carboxyl groups esterified with neomycin in accordance with Example 29 of European patent application EPA 216453 filed on 7th Jul. 1986) and 0.3 g of the 75% esterified partial ethyl ester of hyaluronic acid are added to 150 ml of an aqueous solution containing 7 g of sodium alginate, 10 g of glycerol and 2 g of NaCl. After filtration and degassing, the final solution is extruded and coagulated by the procedure described in Example 1 to obtain 150 g of film with a thickness of 0.250 mm. The film is stored in the solution of glycerol and preservatives described in Example 1. The final neomycin content of the film is 0.00305 g/100 g.

EXAMPLE 7

50 ml of an aqueous dispersion of 10 g of microbeads obtained from mixed ethyl and hydrocortisone ester of hyaluronic acid (Example 15 of European patent application EPA 216453 of 7th Jul. 1986) are added to 150 ml of an aqueous solution containing 7 g of sodium alginate, 10 g of glycerol and 2 g of NaCl. The final dispersion is extruded and coagulated by the procedure described in Example 1 to obtain 150 g of film with a thickness of 0.250 mm. The film is stored in the solution of glycerol and preservatives described in Example 1.

To demonstrate the advantages and activity of the highly hydrated self-supporting film according to the present invention a trial was conducted using 45 male Sprague-Dawley rats of weight 225–250 g. The rats were divided into three groups and were given a heat lesion by a suitable instrument containing a metal prod of known area able to maintain a constant temperature. By applying this instrument to the back of the animal in a region close to the caudal reproducible heat lesions were obtained classifiable as third degree burns.

The treatment scheme involved a group of untreated animals, a group of animals treated conventionally with VASELINE® gauze and a third group treated with a film of hydrated gel as described in Example 1 of the present patent. The medications were changed every 3 days, 5 animals of each group being sacrificed 9, 15 and 25 days after the lesion. After a planimetric evaluation of the lesion area add eschar area, biopsies were taken for histological examination. The results of these tests are given in Table 1.

TABLE 1

|  | day 9 | | | day 15 | | | day 25 | | |
| --- | --- | --- | --- | --- | --- | --- | --- | --- | --- |
|  | NT | GG | G | NT | GG | G | NT | GG | G |
| Persistence of eschar | + | + | + | + | + | ± | + | ± | − |
| Reduction in lesion area | − | − | ± | − | − | + | − | ± | ++ |
| Neoangiogenesis | − | − | + | − | − | ++ | − | − | +++ |

NT = not treated; GG = VASELINE ® gauze; G = gel film
− = not apparent; ± = hardly apparent; + = apparent; ++ = very apparent; +++ = extremely apparent The results summarized in the table show that burns treated with the composition described in Example 1 of the present patent have a positive effect on early eschar fall, reduction in lesion area and neovascularization.

We claim:

1. A hydrated self-supporting gel film for use as wound medication or covering material to be applied in direct contact with the area to be treated in the therapeutic treatment of cutaneous lesions and/or cutaneous pathologies, consisting essentially of a quantity of between 1% and 7.5% of at least one alkaline alginate, between 0.1% and 5% of alkaline earth alginate, between 0.1% and 10% of a polyhydric alcohol and between 0.05% and 10% of a polymer of hydrophilic character selected from the group consisting of hyaluronic acid and derivatives thereof, the remaining constituent being water.

2. The gel film as claimed in claim 1 containing 3.5% of at least one alkaline alginate.

3. The gel film as claimed in claim 1 in which the alkaline alginate is selected from the group consisting of sodium alginate, potassium alginate and ammonium alginate.

4. The gel film as claimed in claim 1 which comprises 1% of calcium alginate.

5. The gel film as claimed in claim 1 which comprises 5% of a polyhydric alcohol.

6. The gel film as claimed in claim 1 in which the polyhydric alcohol is glycerol.

7. The gel film as claimed in claim 1 which comprises 0.5% of the hydrophilic polymer.

8. The gel film as claimed in claim 1 in which the hydrophilic polymer is sodium hyaluronate.

9. The gel film as claimed in claim 1, in which the hydrophilic polymer is hyaluronic acid 75% esterified with ethyl alcohol.

10. The gel film as claimed in claim 1, in which the hydrophilic polymer is the neomycin salt of hyaluronic acid 75% esterified with ethyl alcohol.

11. The gel film as claimed in claim 1, in which the hydrophilic polymer is a mixed total ester of hyaluronic acid, 80% of the carboxy groups being esterified with ethanol and 20% of the carboxy groups being esterified with hydrocortisone.

12. A therapeutic method for treating cutaneous lesions and/or cutaneous pathologies which comprises the application in direct contact to the area to be treated of a hydrated self-supporting gel film of claim 1.

13. The method according to claim 12, wherein the gel film comprises 3.5% of at least one alkaline alginate.

14. The method according to claim 12 wherein the gel film comprises 1% of calcium alginate.

15. The method according to claim 12 wherein the gel film comprises 5% of polyhydric alcohol.

16. The method according to claim 12 wherein the polyhydric alcohol is glycerol.

17. The method according to claim 12 wherein the gel film further comprises 0.5% of the hydrophilic polymer.

18. The method according to claim 12, wherein the gel film further comprises a medicament.

19. The method according to claim 18, wherein the medicament is selected from the group consisting of antiseptic, antibiotic and anti-inflammatory drugs.

20. The method as claimed in claim 18, wherein the medicament quantity is between 0.01% and 10%.

21. The method according to claim 12 wherein the gel film comprises a mixed total ester of hyaluronic acid, 80% of the carboxy groups being esterified with ethanol and 20% of the carboxy groups esterified with hydrocortisone.

22. The method according to claim 12 wherein the polymer of hydrophilic character is hyaluronic acid esterified with ethyl alcohol.

23. The method according to claim 22 wherein the degree of esterification is 75%.

24. The method as claimed in claim 12, wherein the hydrophilic polymer is the neomycin salt of hyaluronic acid 75% esterified with ethyl alcohol.

25. The method as claimed in claim 12, wherein the alkaline alginate is selected from the group consisting of sodium alginate, potassium alginate and ammonium alginate.

26. The method as claimed in claim 12, wherein the hydrophilic polymer is sodium hyaluronate.

27. A hydrated self-supporting gel film for use as wound medication or covering material to be applied in direct contact with the area to be treated in the therapeutic treatment of cutaneous lesions and/or cutaneous pathologies, consisting essentially of a quantity of between 1% and 7.5% of at least one alkaline alginate, between 0.1% and 5% of alkaline earth alginate, between 0.1% and 10% of a polyhydric alcohol, between 0.05% and 10% of a polymer of hydrophilic character selected from the group consisting of hyaluronic acid and derivatives thereof, and between 0.01% and 10% of a medicament, the remaining constituent being water.

28. The gel film as claimed in claim 27 containing 3.5% of at least one alkaline alginate.

29. The gel film as claimed in claim 27 in which the alkaline alginate is selected from the group consisting of sodium alginate, potassium alginate and ammonium alginate.

30. The gel film as claimed in claim 27 which comprises 1% of calcium alginate.

31. The gel film as claimed in claim 27 which comprises 5% of a polyhydric alcohol.

32. The gel film as claimed in claim 27 in which the polyhydric alcohol is glycerol.

33. The gel film as claimed in claim 27 which comprises 0.5% of the hydrophilic polymer.

34. The gel film as claimed in claim 27 in which the hydrophilic polymer is sodium hyaluronate.

35. The gel film as claimed in claim 27, wherein the medicament is selected from the group consisting of antiseptic, antibiotic and anti-inflammatory drugs.

* * * * *